United States Patent
Canova et al.

(10) Patent No.: US 9,421,162 B2
(45) Date of Patent: Aug. 23, 2016

(54) METHODS OF USING POLYMERIC COMPOSITIONS CONTAINING IR-EMITTING ABSORBING ADDITIVES

(71) Applicant: Rhodia Poliamida E Especialidades LTDA, Sao Paulo (BR)

(72) Inventors: Thomas Canova, Sao Paulo (BR); Dany Bizaroli De Mendonca, Sao Paulo (BR); Tarcis Cordeiro Bastos, Sao Paulo (BR)

(73) Assignee: RHODIA POLIAMIDA E ESPECIALIDADES LTDA, Sao Paulo (BR)

( * ) Notice: Subject to any disclaimer, the term of this patent is extended or adjusted under 35 U.S.C. 154(b) by 45 days.

(21) Appl. No.: 13/717,415

(22) Filed: Dec. 17, 2012

(65) Prior Publication Data

US 2013/0122062 A1 May 16, 2013

Related U.S. Application Data

(62) Division of application No. 12/747,631, filed as application No. PCT/IB2008/003429 on Dec. 11, 2008, now Pat. No. 9,044,384.

(30) Foreign Application Priority Data

Dec. 14, 2007 (FR) ...................... 07 08724
Jul. 30, 2008 (FR) ...................... 08 04334

(51) Int. Cl.
| | |
|---|---|
| A61K 31/785 | (2006.01) |
| A61K 9/00 | (2006.01) |
| A61K 8/02 | (2006.01) |
| A61K 8/23 | (2006.01) |
| A61K 8/26 | (2006.01) |
| A61K 8/29 | (2006.01) |
| A61K 8/88 | (2006.01) |
| A61Q 19/06 | (2006.01) |
| C08J 3/22 | (2006.01) |
| D01F 1/10 | (2006.01) |
| D01F 6/60 | (2006.01) |
| A61F 7/00 | (2006.01) |
| A61N 5/06 | (2006.01) |

(52) U.S. Cl.
CPC ............. *A61K 9/0014* (2013.01); *A61K 8/027* (2013.01); *A61K 8/23* (2013.01); *A61K 8/26* (2013.01); *A61K 8/29* (2013.01); *A61K 8/88* (2013.01); *A61K 31/785* (2013.01); *A61Q 19/06* (2013.01); *C08J 3/22* (2013.01); *D01F 1/10* (2013.01); *D01F 1/103* (2013.01); *D01F 6/60* (2013.01); *A61F 2007/0088* (2013.01); *A61K 2800/242* (2013.01); *A61N 2005/066* (2013.01); *C08J 2301/00* (2013.01); *C08J 2323/00* (2013.01); *C08J 2367/00* (2013.01)

(58) Field of Classification Search
None
See application file for complete search history.

(56) References Cited

U.S. PATENT DOCUMENTS

| | | | |
|---|---|---|---|
| 4,999,243 A | 3/1991 | Maeda | |
| 6,316,102 B1 * | 11/2001 | Sasaki | ............. 428/364 |
| 2006/0057053 A1 | 3/2006 | Otobe et al. | |
| 2007/0033696 A1 | 2/2007 | Sellier | |
| 2007/0232486 A1 * | 10/2007 | Aso et al. | ............. 502/208 |
| 2007/0249773 A1 | 10/2007 | Becker et al. | |

FOREIGN PATENT DOCUMENTS

| | | |
|---|---|---|
| CN | 2866527 Y | 2/2007 |
| EP | 0 582 769 A1 | 2/1994 |
| EP | 1 094 136 A1 | 4/2001 |
| EP | 1094136 * | 4/2001 |
| EP | 1 291 405 A1 | 3/2003 |
| EP | 1847635 A1 | 10/2007 |
| FR | 2 865 905 B1 | 8/2005 |
| GB | 2 303 375 A | 2/1997 |
| JP | 63-227828 A | 9/1988 |
| JP | 1-314723 A | 12/1989 |
| JP | 6-41801 A | 2/1994 |
| JP | 10-212663 A | 8/1998 |
| JP | 2002-363821 A | 12/2002 |
| JP | 2004002119 A | 1/2004 |
| KR | 20070041525 A | 4/2007 |
| TW | 422898 | 2/2001 |
| WO | 2007/055432 A1 | 5/2007 |

OTHER PUBLICATIONS

"Cellulite," Le Petit Larouse: Grand Format, 2001, p. 189, Larouse, Paris, France.
Wollina et al., "Esthetic and cosmetic dermatology," Dermatologic Therapy, 2008, p. 118-130, vol. 2.
"Bermuda Anticelulite Invel," Found at : http://pt.shvoong.com/internet-and-technologies/407494-bermuda-anticelulite-invel/, article published 2006 (English language translation provided).

* cited by examiner

Primary Examiner — Bethany Barham
Assistant Examiner — Melissa Javier
(74) Attorney, Agent, or Firm — Dentons US LLP

(57) ABSTRACT

Polymeric compositions containing additives having properties of emission and/or absorption of radiation in the long infrared region, and articles shaped therefrom are produced, including yarns and textile articles such as fabrics or knits; such additives include organic additives or inorganic fillers which have a capacity for absorption/emission of radiation in the infrared region, in a wavelength range of from 2 μm to 20 μm, and also a polymeric substrate, with the proviso that the inorganic fillers may be selected from among oxides, sulfates, carbonates, phosphates and silicates, and such inorganic fillers having an average particle size of less than 2 μm.

14 Claims, 1 Drawing Sheet

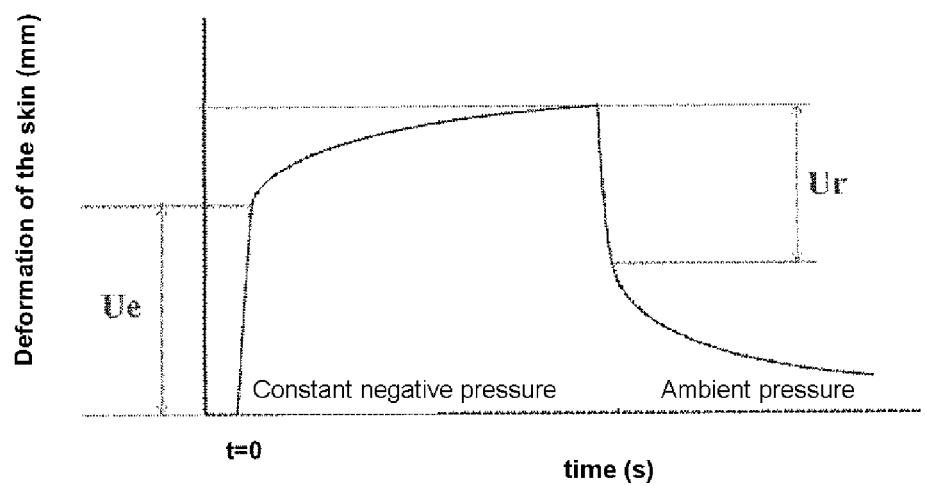

METHODS OF USING POLYMERIC COMPOSITIONS CONTAINING IR-EMITTING ABSORBING ADDITIVES

This application is a divisional of U.S. application Ser. No. 12/747,631, filed Aug. 19, 2010, which is a U.S. National Stage of PCT/IB2008/003429, filed Dec. 11, 2008, which claims priority under 35 U.S.C. §119 to FR 08/04334, filed Jul. 30, 2008, and FR 07/08724, filed Dec. 14, 2007, each hereby expressly incorporated by reference in its entirety and each assigned to the assignee hereof.

The present invention relates to a polymeric composition which comprises the use of additives having properties of emission and/or absorption of radiation in the long infrared range, and also to articles manufactured using this composition.

More specifically, the present invention relates to a polymeric composition which comprises additives having properties of emission of radiation in the infrared region, in a wavelength range of between 2 μm and 20 μm, and also to articles manufactured using this composition. The present invention also relates to methods of manufacturing polyamide compositions and yarns containing these additives, and also to articles such as textile articles, for instance fabrics or knits manufactured using these yarns, and the use of these articles.

The interaction between radiation in the infrared region, having a wavelength of between 2 μm and 20 μm, and biological tissues has attracted the attention of scientists for two decades. According to published studies, infrared radiation in this range leads to biostimulation such as an increase in microcirculation of the blood, a decrease in muscle spasms, an increase in cell metabolism, inter alia. According to one of the mechanisms proposed, the cells of the biological tissues are stimulated by a process of resonance with the radiation, leading to an increase in blood circulation and a decrease in the lactic acid concentration in human skeletal muscles (Niwa et al 1993: Niwa, Y.; Iizawa, O.; Ishimoto, K.; Jiang, X.; Kanoh, T.; *Electromagnetic Wave Emitting products and "Kikoh" Potentiate Human Leukocyte Functions*; International Journal of Biometeorology No. 37, p. 133-138, 1993; Perez and Martinez 1995; Perez, A. C. N., Martinez, A. J. A., *Fibra de Photon Plantino*. Saint Jean de Compostelle, 1993, p. 7-71). Other effects, such as increased peripheral blood flow and increased body temperature, have also been described in the literature.

Over the last few years, patents have been published, claiming the use of materials emitting infrared radiation in the range considered above, for a textile application. In general, the application is directed towards thermal absorption effects (U.S. Pat. No. 5,053,275) and antimicrobial effects (U.S. Pat. No. 6,316,102) and concerns the use of particles of titanium metal (U.S. Pat. No. 7,201,945) or of a composition of oxide, carbide, sulphate and silicate inorganic fillers. The materials mentioned in the patents are applied by means of an aqueous solution (in the case of titanium metal) or else mixed and treated with a type of polymeric resin and deposited by coating (EP 1792724) onto textile surfaces. These surface applications do not give good resistance to wear and to washing, nor a pleasant feeling on contact with the skin, in particular in the form of resin coatings. Some patents seek to solve this problem by incorporating the materials into the polymeric substrate and by producing filaments by means of extrusion, drawing and texturing methods (U.S. Pat. No. 4,999,243, U.S. Pat. No. 5,880,044, WO 2007/055432). However, the use of high levels of oxides and of carbides having a high hardness is not suitable for the production of yarns using thermoplastic components, since they bring about rapid deterioration of machine parts. The solution found also has drawbacks: the coloration of certain carbides and the poor effectiveness of the treatment (frequent breaking of filaments) compromise the mechanical properties of the yarn.

An alternative proposed by patent EP 1094136 concerns the use of a composition of white conductive particles, of infrared-emitting white oxides and of thermoplastic resins for the production of filaments having lower levels of oxides. However, the composition exhibits oxides with a very high hardness (above 8.0 Mohs) and the use of potassium titanate, which is generally in the form of a fibrous powder, that can be categorized as a breathable fibre, makes the handling difficult and disadvantageous from the health and hygiene point of view.

Moreover, cosmetic products which stimulate the skin are always being sought, in particular for individuals who have "cellulite" (gynoid lipodystrophy). In fact, "cellulite" is generally associated with the presence of fatty substances in the fat cells present under the skin, which leads to a distortion of the tissues under the skin, and causes the famous "orange peel" effect. Solutions for reducing cellulite are therefore always being sought. This is in order to improve the comfort and the well-being of the individual.

To this end, it has been found, in the context of the present invention, that additives having properties of emission and/or absorption in the infrared region also interact with another biological tissue, which is the skin. Indeed, these additives make it possible in particular to reduce or even eliminate cellulite, thereby being particularly advantageous.

The present invention relates to the production of a polymeric composition in which the characteristics of the infrared-absorbing and/or -emitting additives (absorbing and/or emitting in a wavelength range between 2 μm and 20 μm) and the amounts used solve the problems stated above regarding the difficulty in treating the inorganic fillers and the yarns, enabling the production of yarns and of textile articles which offer comfort, well-being, improved microcirculation, better thermal homogeneity and reduced muscle fatigue.

The principle objective of the present invention is to obtain yarns, fibres, filaments and articles having properties of blood microcirculation stimulation so as to offer better thermal homogeneity and a decrease in muscle fatigue, and also better elasticity of the skin, through the introduction, into a polymeric matrix, of additives having an infrared emission and/or absorption property, which can be readily handled with ease from an industrial point of view. These articles make it possible in particular to reduce cellulite.

The present invention relates to the use of inorganic fillers and/or organic additives introduced into polymers in order to confer infrared emission properties capable of offering better thermal homogeneity and better elasticity of the skin, and biostimulation for a decrease in muscle fatigue, in order to bring comfort and well-being to the individual; and also to the method for obtaining in particular the fibres, yarns and articles obtained using these polymeric compositions. The polymers used are those spun by melt-spinning, such as polyester, polyamide, polyolefins (and copolymers thereof), inter alia, or through solutions, such as polyacrylic polymers, polyacrylates and copolymers thereof, and cellulose derivatives such as cellulose acetate, cellulose propionate, viscose, etc. The additives may be introduced into the polymer according to any method known to those skilled in the art. Preferably, the introduction is carried out in the polymer synthesis phase, or else in the spinning phase by means of direct mixing of the inorganic fillers and/or organic additives in the molten polymer or in solution, or else through a masterbatch, the use of a combination of two methods of introduction possibly being appropriate.

The composition according to the invention comprises a combination of organic additives or inorganic fillers which have a capacity for emission and/or absorption of infrared radiation in the wavelength range between 2 μm and 20 μm, and of a polymer.

The composition according to the invention exhibits a number of infrared radiation absorption peaks of greater than 10 in the following ten frequency ranges: 3.00+/−0.30 μm, 6.20+/−0.50 μm, 8.00+/−0.25 μm, 8.50+/−0.25 μm, 9.00+/−0.25 μm, 9.50+/−0.25 μm, 10.00+/−0.25 μm, 10.50+/−0.25 μm, 11.00+/−0.25 μm, 14.60+/−2.10 μm, at least 1 peak being present in at least 7 of these ten frequency ranges.

The infrared radiation absorption spectrum of the composition may be determined by any method known to those skilled in the art. One possible method is the use of a Bruker Equinox 55 apparatus, with a resolution of 4 cm$^{-1}$. In this case, the spectrum obtained is in the ATR (Attenuated Total Reflectance) form, using a ZnSe crystal.

Advantageously, the inorganic fillers are of at least one type chosen from oxides, sulphates, carbonates, phosphates and silicates, having a mean particle size of less than 2 μm.

According to the present invention, a polymer composition is provided which includes additives emitting infrared in the wavelength range of between 2 μm and 20 μm. The polymer may be chosen from the group comprising polyesters, polyolefins, polymers based on cellulose ester, such as cellulose acetate, cellulose propionate, rayon, viscose and polymers of the same family, acrylic polymers and copolymers, polyamides, polyhexamethylene adipamide (PA66) or polycaproamide (PA6), or copolymers thereof in any proportions, or else blends of any polymers mentioned above. According to one preferential embodiment, the thermoplastic polymer which makes up the thermoplastic matrix of the polymeric composition is based on a polyamide, chosen from polyamide 6, polyamide 66 and copolymers of polyamide 6/polyamide 66 in any proportions.

Additives have been developed which can be used in the production, for example, of yarns, fibres and filaments having biostimulant properties which offer improved blood microcirculation, better thermal homogeneity, better elasticity of the skin and a decrease in muscle fatigue, resulting in a greater comfort and well-being for the users of the articles containing them, in particular users having cellulite. These articles make it possible to reduce cellulite.

More specifically, the present invention relates, firstly, to the use of a combination of additives in polymeric compositions in order to obtain the effect described above, characterized in that the combination comprises at least one inorganic filler chosen from the oxide group (titanium dioxide, silicon dioxide, magnesium oxide), the sulphate group (barium sulphate, calcium sulphate, strontium sulphate), the carbonate group (calcium carbonate or sodium carbonate), the silicate group (actinolite, tourmaline, serpentine, kaolin and other aluminosilicates) and the phosphate group (zirconium phosphates, apatite, and also other possible phosphates, or else mixtures thereof).

The organic additives may be organic compounds containing silicon, such as organoalkoxysilanes, for example dimethyldiethoxysilane or methyltriethoxysilane. The organic additives may also be organometallic compounds such as, for example, alkylmetal ester, alkylmetal chelate, alkylmetal acylate, metal ester chelate, metal alcoholate, aluminium isopropylate, aluminium sec-butylate or zirconium tetracetylacetonate, preferably aluminium isopropylate, aluminium sec-butylate or zirconium tetraacetylacetonate.

The inorganic fillers used in combination as infrared absorbers and/or emitters in the wavelength range of between 2 μm and 20 μm are in the form of particles having a size of less than 2 μm, preferably less than 1 μm, and advantageously less than 0.5 μm. The particles may be advantageously covered or coated so as to make them inert with respect to the components into which they will be incorporated, or else so as to provide better compatibility with the polymeric substrate, without this interfering in their characteristic of absorbing and/or emitting infrared in the range under consideration.

Combinations of two inorganic fillers, or of three inorganic fillers, are preferred, and in particular the ternary combinations can be chosen from those which comprise titanium dioxide, barium sulphate, silicon dioxide and a filler of the silicate group.

Even more particularly, the combination comprises three inorganic fillers as a mixture in any proportions, such as those chosen from the group comprising: titanium dioxide/silicon dioxide/tourmaline; titanium dioxide/silicon dioxide/barium sulphate; and titanium dioxide/barium sulphate/tourmaline. Titanium dioxide/barium sulphate/tourmaline is preferably used.

According to the present invention, the combination of inorganic fillers described above is used as additive emitting infrared in the range of 2 μm to 20 μm in polymeric compositions for the production of yarns, fibres, filaments and textile articles.

According to one particular embodiment of the invention, the additive is present in an amount of less than 9.0% of additive relative to the total mass of the polymer composition, preferably less than 6.0%, advantageously less than 4.5% by weight. Similarly, according to another particular embodiment of the invention, the proportion by weight of the combination of inorganic fillers relative to the total weight of polymeric composition is greater than 1.0%, preferably greater than or equal to 1.5%, and even more preferably greater than or equal to 2.5%.

The polymer composition may also contain an agent that is antimicrobial or bacteriostatic, fire-repellent, stabilizing against UV rays, and also other agents known to those skilled in the art.

According to the present invention, it is possible to use a combination of additives, such as that described above, in any proportions. By way of example, and in a nonlimiting manner, the inorganic fillers of the ternary combinations will be realized, in the use of the present invention, in proportions advantageously ranging from 80:10:10 to 10:30:60, more specifically in proportions of 50:25:25.

Another subject of the present invention is the method for preparing the polymeric compositions with a combination of far-infrared-absorbing/-emitting inorganic fillers, as defined above. The fillers or additives may be introduced into the polymeric composition according to any method known to those skilled in the art. Preferably, the introduction is carried out during the polymer synthesis phase, or by direct mixing with the polymer during the filament spinning phase, or else by means of a concentrate of particles in the form of a masterbatch, subsequently diluted to predetermined concentrations in the polymeric mass during the spinning phase.

The inorganic fillers or organic additives may be added separately according to one or more methods of introduction described above.

The masterbatch is prepared with amounts of inorganic filler of advantageously between 10% and 65% by weight relative to its total mass, preferably between 15% and 35%, even more preferably between 15% and 25%.

The present invention also relates to the articles, and in particular to the yarns, fibres and filaments, obtained using the compositions described above, in which the combination of the inorganic fillers or organic additives of the present invention has been used.

In the case of yarns, fibres and filaments obtained by melt-spinning, the additivated thermoplastic composition is obtained with the introduction of the inorganic fillers or organic additives into the molten polymer by means of a mixing device, for example upstream of a spinning device. Continuous multifilament yarns, monofilaments, short and long fibres, or mixtures thereof, can be obtained through the spinning of the additivated thermoplastic composition. The yarns, fibres and filaments obtained using the polymeric compositions presented in the present invention may be subjected to all the textile treatments known to those skilled in the art, such as extrusion, drawing, texturing, dyeing, finishing, etc.

The present invention also relates to the articles obtained from the yarns, fibres and filaments described above. The articles may be obtained from a single type of yarn, fibre or filament, or from a mixture of yarns, fibres or filaments of different types.

The term "articles" is intended to mean, in particular, fabrics, knits and nonwovens. The article may be composed of at least one type of yarn, filament or fibre obtained from polymeric compositions described in the present invention.

The article may be a film or a powder obtained from the composition described above. The film or the powder may be obtained according to any method known to those skilled in the art.

The present invention also relates to the use of an article, in particular textile, as described above, based on a composition as described above, for stimulating biological tissues, in particular biological tissues of physically active individuals. Advantageously, the biological tissue is the skin, in particular the skin of individuals having cellulite. According to one particular embodiment of the invention, the invention relates to such a use for decreasing cellulite in individuals.

Advantageously, the invention relates to such a use for stimulating the blood microcirculation.

Everything that was described above regarding the polymeric composition of the invention and the articles of the invention applies here for the use of the invention.

BRIEF DESCRIPTION OF THE DRAWINGS

FIG. 1 shows the elasticity of the skin when negative pressure is applied and when negative pressure is no longer applied.

The following examples presented by way of indication will make the advantages of the present invention clearly apparent.

EXAMPLES

The samples of Examples 1 to 6 below were prepared with a polyamide 66 having a relative viscosity (RV) of 43, measured in a solution of formic acid at 90% in water. The incorporation of infrared-emitting inorganic fillers into the polyamide 66 was carried out through the mixing of the inorganic fillers in powdered form and the triturated polymer, in a proportion of 20% by weight of inorganic filler for obtaining a masterbatch. The mixture was extruded, cooled and granulated. The masterbatch thus obtained was introduced into the polyamide 66 during the spinning phase. The molten polymeric composition was spun at a temperature of between 280° C. and 300° C. (measured in the die), air-cooled (20° C., relative humidity of 65%) and wound at a speed of 4200 m/min so as to obtain a continuous multi-filament yarn. The multifilament yarn made up of 68 filaments with a circular cross section was subsequently textured. The titre of the filament in the finished product is 1.2 dtex. The yarn thus obtained was used in the production of knits for the preparation of Bermuda shorts and tee-shirts, by using a circular knitting machine. The tee-shirts thus obtained have a surface density of 175 g/m², and the Bermuda shorts have a surface density of 305 g/m², and contain 12% of spandex. These articles were subsequently used to evaluate the effectiveness of the compositions.

Example 1

A sample of a yarn of polyamide 66 containing 1.5% of $TiO_2$ and 0.5% of $BaSO_4$ was prepared according to the previous description. The heat variation of the body (trunk and lower limbs) of two groups of 15 athletes subjected to the application of a physical activity protocol (ergometric test on a treadmill according to the Bruce protocol) was compared. The test was carried out over the course of three days:

on day 1, the athletes were subjected to the Bruce protocol, clothed in an outfit comprising a cotton tee-shirt and polyester Bermuda shorts, this being known as the control group, for the definition of the maximum time (t) (defined as the duration of physical activity until a certain heart rate or arterial pressure limit—predefined according to the individual's age—is reached, or until the athlete asks to stop owing to fatigue);

on day 2, the athletes did not perform any physical activity;

on day 3, the same athletes were subjected to the Bruce protocol until the time (t) was reached, while clothed in the outfit comprising tee-shirt and Bermuda shorts, this being referred to as the sample group;

samples evaluated: cotton and polyamide 66 containing 1.5% of $TiO_2$ and 0.5% of $BaSO_4$.

The body temperature was measured by means of the thermography technique (Raytec Fluke TiSO Thermal Image equipment) before and after the application of the protocol, and the index of thermal variation $\Delta T/\Delta T1$ was evaluated.

The index of thermal variation was obtained by comparing the mean temperatures before (initial temperature) and after (final temperature) the physical activity protocol was carried out:

$$\Delta T = \Delta T2 - \Delta T1$$

where:

$$\Delta T1 = T_{fc} - T_{ic}$$

(subtraction between the mean final $T_{fc}$ and initial $T_{ic}$ temperatures of the control group), and $$\Delta T2 = T_{fe} - T_{ie}$$

(subtraction between the mean final $T_{fe}$ and initial $T_{ie}$ temperatures of the sample group).

Table 1 below summarizes the indices of thermal variation $\Delta T/\Delta T1$ obtained in the regions of the trunk and lateral part of the leg for group A (athletes clothed in tee-shirt and Bermuda shirts made of cotton) and group B (athletes clothed in tee-shirt and Bermuda shorts made of PA66 containing 1.5% of $TiO_2$ and 0.5% of $BaSO_4$).

TABLE 1

| Group | Sample | Trunk ΔT/ΔT1 (%) | Lateral part of the leg ΔT/ΔT1 (%) |
|---|---|---|---|
| A | Cotton | 38 | 48 |
| B | Polyamide 66 + $TiO_2$ + $BaSO_4$ | 48 | 62 |

The indices obtained show an evaluation of the temperature in group B compared with group A, indicating an increase in blood circulation when the articles made of additivated polyamide are used.

Example 2

A sample of a yarn of polyamide 66 containing 1.5% of $TiO_2$ and 0.5% of $BaSO_4$ was prepared according to the previous description and compared with a sample of polyamide yarn containing 1.5% of $TiO_2$. The heat variation of the body (trunk and lower limbs) of two groups of 15 athletes subjected to the application of a physical activity protocol (ergometric treadmill test according to the Bruce protocol) was compared. The test and the temperature measurement were carried out as described in Example 1.

The thermal heterogeneity index (h) was obtained by calculating the variation in deviation of the temperature measurements on the region under consideration, following the application of the physical activity protocol:

$$h=(d2-d1)/d1$$

where,
d1=standard deviation of the temperature of the control group, and
d2=standard deviation of the temperature of the sample group.

Table 2 below summarizes the thermal heterogeneity index (h) obtained in the regions of the lower trunk and the lateral part of the leg for group C (athletes clothed in tee-shirt and Bermuda shorts made of yarn of polyamide 66 containing 1.5% of $TiO_2$ and group D (athletes clothed in tee-shirt and Bermuda shorts made of yarn of polyamide 66 containing 1.5% of $TiO_2$ and 0.5% of $BaSO_4$).

TABLE 2

| Group | Sample | h (%) |
|---|---|---|
| C | Polyamide 66 containing 1.5% of $TiO_2$ | 20 |
| D | Polyamide 66 $TiO_2$ + $BaSO_4$ | 14 |

The results of Table 2 above show a greater homogeneity for group D (smaller thermal heterogeneity index), attesting to the influence of the additive promoting body temperature homogeneity.

Example 3

A sample of a yarn of polyamide 66 containing 1.5% of $TiO_2$, 0.5% of $BaSO_4$ and 0.2% of tourmaline was prepared according to the previous description. The concentration of lactate (L) in the blood of two groups of 15 athletes was evaluated before and after the application of a physical activity protocol comprising an ergometric treadmill test according to the Bruce protocol. The lactate concentration (in mmol/liter) was obtained by means of the strip test analysis (Accutrend lactate equipment from Roche Diagnóstica Brazil).

The test was carried out according to the steps described in Example 1, with samples of polyester and polyamide 66 containing 1.5% of $TiO_2$, 0.5% of $BaSO_4$ and 0.2% of tourmaline, and the lactate variation index ΔL/ΔL1 was calculated:

$$\Delta L = \Delta L2 - \Delta L1$$

where:

$$\Delta L1 = L_{fc} - L_{ic}$$

(subtraction between the final lactate $L_{fc}$ and initial lactate $L_{ic}$ concentrations of the control group),
and $$\Delta L2 = L_{fe} - L_{ie}$$

(subtraction between the final lactate $L_{fe}$ and initial lactate $L_{ie}$ concentrations of the sample group).

Table 3 below shows the index of variation in lactate concentration ΔL/ΔL1 obtained for group E (athletes clothed in tee-shirt and Bermuda shorts made of polyester) and group F (athletes clothed in tee-shirt and Bermuda shorts made of PA66 containing 1.5% of $TiO_2$, 0.5% of $BaSO_4$ and 0.2% of tourmaline).

TABLE 3

| Group | Sample | ΔL/L1 (%) |
|---|---|---|
| E | Polyester | −31 |
| F | Polyamide 66 + $TiO_2$ + $BaSO_4$ + tourmaline | −36 |

The results show a decrease in lactate concentration in the blood, which is 5% greater in group F, compared with group E. The lactate level in the blood is directly associated with the muscle fatigue.

Example 4

A sample of a yarn of polyamide 66 containing 1.5% of $TiO_2$, 0.5% of $BaSO_4$ and 0.2% of tourmaline was prepared according to the previous description and compared with a sample of a yarn of polyamide containing 1.5% of $TiO_2$. The thermal variation of the regions of the lower trunk and lateral part of the leg of a group of 15 athletes subjected to the application of a physical activity protocol (ergometric treadmill test at a constant speed of 6.5 km/h and an incline of 6% for 30 minutes) was evaluated, for comparison. The test was carried out over the course of three days:

on day 1, the athletes were subjected to the protocol while clothed in Bermuda shorts prepared with a yarn of polyamide 66 containing 1.5% of $TiO_2$, 0.5% of $BaSO_4$ and 0.2% of tourmaline;
on day 2, the athletes did not perform any physical activity;
on day 3, the athletes were subjected to the protocol while clothed in Bermuda shorts prepared with a yarn of polyamide 66 containing 1.5% of $TiO_2$.

The body temperature was measured by means of the thermography technique (Raytec Fluke TiSO Thermal Image equipment) before and after the application of the protocol, and the thermal heterogeneity index was evaluated.

The thermal heterogeneity index (h) was obtained by calculating the variation in the deviation of the temperature measurements in the region under consideration, before and after the application of the physical activity protocol:

$$h=(d2-d1)/d1$$

where,
d1=standard deviation of the temperature before the application of the physical activity protocol, and
d2=standard deviation of the temperature after the application of the physical activity protocol.

TABLE 4

| Sample | h (%) |
|---|---|
| Polyamide 66 containing 1.5% of TiO$_2$ | 30 |
| Polyamide 66 TiO$_2$ + BaSO$_4$ + tourmaline | 20 |

The results of Table 4 above show a greater homogeneity for the sample of polyamide 66 containing TiO$_2$, BaSO$_4$ and tourmaline (smaller thermal heterogeneity index), attesting to the influence of the additive promoting body temperature homogeneity.

The increase in blood circulation, the decrease in the level of lactate in the blood and the better thermal homogeneity are associated with a decrease in muscle fatigue. Thus, the results presented in the examples above indicate a decrease in muscle fatigue in connection with the use of the article produced with the yarns of polyamide additivated through the use of far-infrared-emitting inorganic fillers or organic additives defined in the present invention.

Examples 5 and 6

A sample of a yarn of polyamide 66 containing 1.5% of TiO$_2$ (Example 5), and a sample of a yarn of polyamide 66 containing 1.5% of TiO$_2$, 0.5% of BaSO$_4$ and 0.2% of tourmaline (Example 6), were prepared according to the previous description.

Thermal Homogeneity of the Skin

The thermal variation of the skin (on a region comprising the outer side, the front and the rear of the thigh and of the buttock) of a group of 15 volunteers having worn, for 60 days, 6 hours a day, a pair of Bermuda shorts of which one leg was manufactured using the yarn of Example 5 and the other leg was manufactured using the yarn of Example 6, was measured. The 15 volunteers exhibit a degree of cellulite I or II on the Nurnberger-Muller scale (reference: Nurnberger F, Muller G. So-called cellulite: an invented disease. J Dermatol Surg Oncol 1978; 4: 221-229).

The body temperature was measured by means of the thermography technique (Raytec Fluke TiSO Thermal Image equipment) before and after the 60 days.

The thermal heterogeneity index (h) was obtained by calculating the ratio between the standard deviations of temperature on the region under consideration, before and following the wearing of the Bermuda shorts for 60 days:

$$h=X_2/X_1$$

where,
X$_1$=standard deviation of the temperature on the region (mean of the standard deviations for the 15 volunteers) before the 60 days, and
X$_2$=standard deviation of the temperature on the region (mean of the standard deviations for the 15 volunteers) after the 60 days.

Table 5 below summarizes the thermal heterogeneity index (h) obtained for the yarn of polyamide 66 containing 1.5% of TiO$_2$ and for the polyamide 66 containing 1.5% of TiO$_2$, 0.5% of BaSO$_4$ and 0.2% of tourmaline.

TABLE 5

| Sample | h (%) |
|---|---|
| Polyamide 66 containing 1.5% of TiO$_2$ | 0.84 |
| Polyamide 66 TiO$_2$ + BaSO$_4$ + tourmaline | 0.67 |

The results of Table 5 above show that there was a 33% decrease in the thermal heterogeneity following the wearing of the Bermuda shorts, for the yarn of polyamide 66 containing 1.5% of TiO$_2$, 0.5% of BaSO$_4$ and 0.2% of tourmaline, and a 16% decrease in the thermal heterogeneity following the wearing of the Bermuda shorts, for the yarn of polyamide 66 containing 1.5% of TiO$_2$. These results show the influence of the additive promoting body temperature homogeneity.

Elasticity of the Skin

In addition to the thermal variation of the body, the variation in elasticity of the skin of the same group of volunteers (on a region comprising the outer side, the front and the back of the thigh and of the buttock) is also measured before and after the 60 days.

The elasticity of the skin was measured using the Cutometer MPA580 apparatus sold by the company CK Electronic GmbH, which uses the principle of the suction method. A negative pressure is created in the apparatus and the skin is drawn into the aperture of the probe. Inside the probe, the depth of penetration of the probe is measured. The ability of the skin to return to its initial position when the negative pressure is no longer applied (elasticity) is measured and expressed by means of a curve (see FIG. 1).

The elasticity of the skin corresponds to the ratio $R=U_r/U_e$, the values of $U_r$ and of $U_e$ corresponding to the values indicated in FIG. 1.

The variation in elasticity F corresponds to $F=[(R_f-R_i)/R_i]\times 100$, with $R_i$, corresponding to the elasticity before the 60 days, and $R_f$ being the elasticity after the 60 days.

Table 6 below summarizes the variation in elasticity F obtained for the yarn of polyamide 66 containing 1.5% of TiO$_2$ and the polyamide 66 containing 1.5% of TiO$_2$ (Example 5) and 0.5% of BaSO$_4$ and 0.2% of tourmaline (Example 6).

TABLE 6

| Sample | F (%) |
|---|---|
| Polyamide 66 containing 1.5% of TiO$_2$ | 1 |
| Polyamide 66 TiO$_2$ + BaSO$_4$ + tourmaline | 8 |

The results of Table 6 above show a significant increase in elasticity for the yarn of polyamide 66 containing 1.5% of TiO$_2$, 0.5% of BaSO$_4$ and 0.2% of tourmaline compared with the yarn of polyamide 66 containing 1.5% of TiO$_2$. These results show the influence of the additive promoting increased elasticity of the skin and therefore a reduction in cellulite.

The increase in elasticity of the skin and the better thermal homogeneity are associated with a better comfort and well-being, and with a decrease in cellulite. Thus, the results presented in the examples above indicate a better comfort and well-being in connection with the use of the article produced with the yarns of polyamide additivated through the use of far-infrared-emitting inorganic fillers or organic additives defined in the present invention.

Antibacterial Activity

The antibacterial activity is measured according to standard JIS L 1902: 2002 on *Staphylococcus aureus* ATCC 6538P and *Klebsiella pneumoniae* ATCC 4352 bacteria for yarns of polyamide 66 containing 1.5% of $TiO_2$, 0.5% of $BaSO_4$ and 0.2% of tourmaline (Example 6):

Said activity is also compared to yarns of cotton having no additive. The tests are carried out on knitted surfaces of 0.4 g.

The different surfaces of the samples are brought into contact with the same number of bacteria, for incubation at 37° C. for 18 hours. At the time t=0 and t=18 h, the number of bacteria is counted.

After verification that the bacteria are growing correctly in the control samples, the mean number of active bacteria immediately after the inoculation on the various samples and the mean number of active bacteria after 18 hours of incubation on the various samples are determined, for each sample, in CFU (Colony Forming Units).

The specific bacteriostatic activity S corresponding to the difference between the logarithm of the mean number of active bacteria after 18 hours of incubation on the control sample (cotton yarns without additive) and the logarithm of the mean number of active bacteria after 18 hours of incubation on the sample (polyamide 66 yarns of Example 6) is then measured.

The results are expressed in Table 7:

TABLE 7

| | Specific bacteriostatic activity S1 (*Staphylococcus aureus*) | Specific bacteriostatic activity S2 (*Klebsiella pneumoniae*) |
|---|---|---|
| Yarns of Example 6 | 0.76 | 0.48 |

The results of Table 7 above show good bacteriostatic activity of the yarns of polyamide 66 containing 1.5% of $TiO_2$, 0.5% of $BaSO_4$ and 0.2% of tourmaline. These results are very advantageous for articles, in particular textile articles, which are in contact with the skin.

Examples 7 and 8

The samples of the examples below were prepared with a polyamide 66 having a relative viscosity (RV) of 43, measured in a solution of formic acid at 90% in water. The incorporation of the $TiO_2$ and of the tourmaline into the polyamide 66 is carried out by introducing these fillers during the polyamide 66 polymerization process, in the form of an aqueous suspension of $TiO_2$ at 20% and of an aqueous suspension of tourmaline at 39%. The incorporation of the $BaSO_4$ into the polyamide 66 was carried out through the mixing of the inorganic fillers in powdered form and of the polyamide 66, in a proportion of 20% by weight of $BaSO_4$ for obtaining a masterbatch. The mixture was extruded, cooled and granulated. The masterbatch thus obtained was introduced into the polyamide 66 during the spinning phase. The molten polymeric composition was spun at a temperature of between 280° C. and 300° C. (measured in the die), air-cooled (20° C., relative humidity of 65%) and wound at a speed of 4200 m/min so as to obtain a continuous multifilament yarn. The multifilament yarn made up of 68 filaments with a circular cross section was subsequently textured. The titre of the filament in the finished product is 1.2 dtex. The yarn thus obtained was used in the production of knits for the preparation of Bermuda shorts, by using a circular knitting machine. The Bermuda shorts thus obtained have a surface density of 305 $g/m^2$, and contain 12% of spandex. These articles were subsequently used to evaluate the effectiveness of the compositions.

A sample of a yarn of polyamide 66 containing 1.5% of $TiO_2$ (Example 7) and a sample of a yarn of polyamide 66 containing 1.5% of $TiO_2$, 0.5% of $BaSO_4$ and 0.2% of tourmaline (Example 8) were prepared according to the previous description.

The blood microcirculation in proximity to the skin was evaluated by ultrasound using the Power Doppler method. The Doppler effect is a change in frequency of the ultrasound reflected by the moving blood cells.

The tests were carried out on a group of 15 volunteers (having a body mass index of 23+/−4 $kg/m^2$) having worn, for 60 days, 6 hours a day, a pair of Bermuda shorts of which one leg was manufactured using the yarn of Example 8 (right leg) and the other leg was manufactured using the yarn of Example 7 (left leg).

The Power Doppler method measures the amplitude of the Doppler signals, directly correlatable to the speed/intensity of the blood flow in the region evaluated. The results obtained were processed with a 95% confidence interval.

The increase in the Doppler signal D % is measured, between the time t0 (initial) and t60 (after 60 days).

It corresponds to the following equation:

$$D\% = \frac{\left[\frac{\sum_{i=1}^{15}(Dt60_i - Dt0_i)}{n}\right]}{\left[\frac{\sum_{i=1}^{15}(Dt0_i)}{n}\right]}$$

in which D is the Doppler signal, and n is equal to 15 (number of volunteers).

TABLE 8

| Example | Mean increase in Doppler signal D (%) |
|---|---|
| 7 | 31.1 |
| 8 | 92.0 |

An increase in the blood microcirculation is confirmed for the two examples.

The knit prepared using yarns of polyamide 66 containing 1.5% of $TiO_2$, 0.5% of $BaSO_4$ and 0.2% of tourmaline is approximately 3 times better than that prepared using yarns of polyamide 66 containing 1.5% of $TiO_2$.

The results indicated here show that the increase in blood microcirculation is associated with the use of a knit prepared using a polyamide modified with inorganic or organic fillers absorbing/emitting in the far-infrared range, described in the present invention.

The composition of Example 8 exhibits the following infrared radiation absorption properties:

number of peaks in the frequency range 3.00+/−0.30 µm: 2 number of peaks in the frequency range 6.20+/−0.50 µm: 2 number of peaks in the frequency range 8.00+/−0.25 µm: 1 number of peaks in the frequency range 8.50+/−0.25 µm: 1 number of peaks in the frequency range 9.00+/−0.25 µm: 0 number of peaks in the frequency range 9.50+/−0.25 µm: 1 number of peaks in the frequency range 10.00+/−0.25 µm: 0 number of peaks in the frequency range 10.50+/−0.25 µm: 2 number of peaks in the frequency range 11.00+/−0.25 µm: 0 number of peaks in the frequency range 14.60+/−2.10 µm: 3.

The invention claimed is:

1. A method for reducing muscle fatigue comprising contacting the skin of an individual with an article which comprises a polymeric composition comprising a polymer and a combination of three inorganic fillers, wherein the three inorganic fillers are titanium dioxide, barium sulfate, and tourmaline, wherein the amount of the combination of the three inorganic fillers is greater than 1.0% and less than 9.0% by weight relative to the total mass of the polymeric composition, and wherein the combination of inorganic fillers comprises from 10 to 80% by weight of titanium dioxide and from 10 to 30% by weight of barium sulfate relative to the total mass of the three inorganic fillers.

2. The method according to claim 1, wherein the polymer is selected from the group consisting of polyesters, polyolefins, cellulosic polymers, acrylic polymers, polyamides, copolymers thereof, and blends thereof.

3. The method according to claim 2, wherein the cellulosic polymers are selected from the group consisting of cellulose acetates, cellulose propionates, rayons, and viscoses.

4. The method according to claim 2, wherein the polymer is a polyamide or a polyamide copolymer.

5. The method according to claim 4, wherein the polymer is selected from the group consisting of polyamide 6, polyamide 66, and polyamide 6/polyamide 66 copolymers.

6. The method according to claim 1, wherein the inorganic fillers of the polymeric composition have a particle size of less than 2.0 µm.

7. The method according to claim 6, wherein the inorganic fillers of the polymeric composition have a particle size of less than 1.0 µm.

8. The method according to claim 1, wherein the proportion by weight of the three inorganic fillers is between 80:10:10 and 10:30:60.

9. The method according to claim 1, wherein the proportion by weight of the combination of inorganic fillers relative to the total weight of the polymeric composition is greater than or equal to 2.5%.

10. The method according to claim 1, wherein the proportion by weight of the combination of inorganic fillers relative to the total weight of the polymeric composition is less than 6%.

11. The method according to claim 10, wherein the proportion by weight of the combination of inorganic fillers relative to the total weight of the polymeric composition is less than 4.5%.

12. The method according to claim 1, wherein the article is a textile article in the form of yarns, fibres, filaments, or a mixture thereof.

13. The method according to claim 1, wherein the article is a fabric, a nonwoven, a knit, a film, or a powder.

14. A method for reducing the level of lactate in the blood of an individual comprising contacting the skin of the individual during physical activity with an article which comprises a polymeric composition comprising a polymer and a combination of three inorganic fillers, wherein the three inorganic fillers are titanium dioxide, barium sulfate, and tourmaline, wherein the amount of the combination of the three inorganic fillers is greater than 1.0% and less than 9.0% by weight relative to the total mass of the polymeric composition, and wherein the combination of inorganic fillers comprises from 10 to 80% by weight of titanium dioxide and from 10 to 30% by weight of barium sulfate relative to the total mass of the three inorganic fillers.

* * * * *